United States Patent [19]

Balazs et al.

[11] Patent Number: 4,487,865
[45] Date of Patent: Dec. 11, 1984

[54] POLYMERIC ARTICLES MODIFIED WITH HYALURONATE

[75] Inventors: Endre A. Balazs, Riverdale, N.Y.; David J. Wedlock, Cheshire, England; Glyn O. Phillips, Mold, Wales

[73] Assignee: Biomatrix, Inc., Ridgefield, N.J.

[21] Appl. No.: 561,817

[22] Filed: Dec. 15, 1983

[51] Int. Cl.³ .............................................. C08F 8/00
[52] U.S. Cl. ...................................... 524/29; 424/81; 525/54.2
[58] Field of Search ................... 525/54.2; 424/78, 81, 424/82, 83; 524/29

[56] References Cited

U.S. PATENT DOCUMENTS 4,272,522  6/1981  Balazs .................................... 424/94
4,349,467  9/1982  Williams ............................. 525/54.2
4,415,490  11/1983  Joh .................................... 525/54.2

Primary Examiner—Paul R. Michl
Attorney, Agent, or Firm—Sheldon Palmer

[57] ABSTRACT

Polymeric materials (and articles made therefrom) including polyurethanes, polyesters, polyolefins, polyamides, polysiloxanes, vinylic and acrylic polymers are rendered biocompatible by including with the polymeric material hyaluronic acid or a salt thereof. The hyaluronic acid may be coated onto the surface of the polymeric material, dispersed throughout the body of the polymeric material, or both. The hyaluronic acid on the surface of the polymeric material may optionally be cross-linked. The biocompatible polymeric materials are used in the making of various prosthetic devices including heart valves, intraocular lenses, vascular grafts, pacemaker leads and the like.

5 Claims, No Drawings

POLYMERIC ARTICLES MODIFIED WITH HYALURONATE

BACKGROUND OF THE INVENTION

1. Field of the Invention

The present invention relates to acrylic polymeric articles modified with hyaluronic acid ("HA"), and having improved biocompatibility which enables the modified articles to be used in numerous in vivo applications, such as various prosthetic devices including artificial heart valves, vascular grafts, etc.

2. The Prior Art

Hyaluronic acid is a known, naturally occurring material which has many applications in medicine and biology. See, for example, E. A. Balazs U.S. Pat. No. 4,272,522 and publications cited therein.

SUMMARY OF THE INVENTION

The present invention is directed to polymeric articles, and specifically, articles made of acrylic polymers, modified with hyaluronic acid (a substance which is normally present in animal tissues) so as to confer on such articles a considerably higher degree of biocompatibility than the unmodified articles. The invention includes polymeric articles such as castings, films, fibers and fabrics which contain hyaluronic acid or salts thereof dispersed throughout the article or as a coating on the surface thereof, or both. The hyaluronic acid may also be cross-linked after preparation of the article. The thusly modified polymeric articles are therefore quite suitable for use in various prosthetic devices such as artificial heart valves, intraocular lenses, vascular grafts, pacemaker leads and the like, as well as in various kinds of drug delivery systems.

The polymers which can be modified with hyaluronic acid in accordance with the invention include: acrylic polymers such as poly (hydroxyethyl), methacrylate and copolymers of methyl acrylate, and methyl methacrylate.

There are numerous methods of introducing the hyaluronic acid into a polymer or applying it onto the surface of a polymer. One method involves dissolving hyaluronic acid in an appropriate solvent and mixing the obtained solution with a polymer solution or an emulsion and thereafter forming an article, for example a film, from the mixture or applying this mixture as a coating. The suitable solvents for dissolving hyaluronic acid are water, dimethylsulfoxide and dimethylformamide. The surface of the polymeric substrate may be activated, as can the hyaluronic acid.

Another method involves adding hyaluronic acid in a solid form, preferably as a powder, to a polymer solution and thereafter forming an article, for example a film, from the obtained mixture or applying this mixture as a coating.

Still another method involves coating a particulate material with hyaluronic acid from solution and introducing the coated particles into a polymer solution and then forming an article, for example a film, from the obtained mixture or applying this mixture as a coating. Examples of suitable particulate materials are ion exchange resins, silica, alumina, etc.

Finally, in any of the methods described above, the hyaluronic acid can be cross-linked before or after mixing with the polymer with the use of various cross-linking agents.

DETAILED DESCRIPTION OF THE INVENTION

The following examples (wherein all parts given are by weight unless otherwise specified) illustrate the several embodiments of the invention, without however being a limitation thereof, the invention being solely defined by the claims.

EXAMPLE 1

A Polyurethane Based Composition With Hyaluronate Bonded To The Surface And Having Improved Biocompatability Properties Sodium hyaluronate (Na-HA) is activated using the cyanogen bromide method, which has been used to attach proteins and polypeptides to cellulose or Sephadex (Cafe, M. C., Pryce, N. and Robb, I. D. Polymer [1976] 17, 91).

0.1 g of NaHA was dissolved in 40 ml of distilled water. 0.04 g of CNBr was dissolved in 2 ml of distilled water. The cyanogen bromide solution was added to the NaHA solution and the mixture was stirred for 4 hours at room temperature, while keeping the pH constant at 11 by periodic inspection using a pH meter. To this activated NaHA solution, polyurethane samples were added and the solution left a further 18 hours at room temperature and at pH 11.

The presence of hyaluronate on the surface of the polyurethane was established by staining with Methylene Blue dye after repeated washings with distilled water.

EXAMPLE 2

In this example, an improved polyurethane article was prepared which consists of a polyurethane matrix with sodium hyaluronate distributed throughout the body and on the surface of that matrix.

A 7% solution of Polyetherurethane (80AE) (PEUU) was prepared by shaking the polymer in dimethylformamide (DMF). A sodium hyaluronate (NaHA) solution in dimethylsulphoxide and water was prepared by taking 2-8 mg of Na-HA, preswelling with approximately 0.75 ml of distilled water or just sufficient to wet it and leave no supernatant, allowing to stand for 10-15 minutes and then adding 20-25 ml of dimethysulphoxide (DMSO) to give a clear viscous solution of sodium hyaluronate. The PEUU solution in DMF was added to the DMSO solution of Na-HA in the ratio of 1 to 0.7, and if any precipitation occurred the solution was warmed to 40°-50° C. The mixed solution was cast into a glass petri dish and dried in a fan oven at 60° C. for 18 hours.

EXAMPLE 3

In this example, an improved polyurethane article was prepared which consists of sodium hyaluronate distributed throughout a polyurenthane matrix and on the surface of that matrix. The resulting article has improved wetting properties and biocompatability properties.

A polyurethane was dissolved in DMF to give a 10% solution. Lithium bromide was added to the solution of polyurethane in DMF to a level of 10-15% by weight of the polyurethane. The solution was then cast on a glass dish and dried in a fan oven at 60° C. The film was then removed and further placed in a vacuum oven at <1 torr for 24 hours to remove excess DMF. The film was then washed with distilled water until the washings were shown to be free of bromide ion by the silver nitrate test. When this was done the film was coated with a solution of CN-Br activated Na-HA (21 mg in 5 cm$^3$ of 0.2 M NaCl). This was allowed to stand for 3 hours to allow penetration of the polyurethane matrix by the activated Na-HA. The pH of the solution was then dropped by adding $10^{-3}$ M HCl. Incorporation of Na-HA occurred by covalent bonding to the polyurethane surface and by cross linking under the low Ph conditions.

EXAMPLE 4

In this example, a non-covalently cross-linked hydrogel containing sodium hyaluronate in a hydrogel matrix of poly (2-hydroxyethyl methacrylate) was prepared. The sodium hyaluronate is distributed throughout the matrix of the hydrogel and on the surface of the hydrogel. This material has improved elastic properties and biocompatability properties over the same material not containing sodium hyaluronate.

1 g of a linear poly (2-hydroxyethyl methacrylate) (p-HEMA), polymer preparation was used. The polymer was preswelled with the minimum of distilled water for 10–15 minutes. The preswelled p-HEMA was then slowly covered with ethanol, with stirring until a total of 20 ml had been added, resulting in a viscous solution. This was then centrifuged to remove any undissolved p-HEMA or other insoluble matter. 2–4 mg of Na-HA was preswelled, then dissolved in 10 ml of distilled water. An equal volume of ethanol was then added. The p-HEMA solution and Na-HA solutions were then added to each other and the mixture either cast into glass dishes and dried in a fan oven at 60° C. to give films, or applied to a rotating glass mandril (silicon coated) and dried by evaporation in a warm air stream to give tubing. The dried polymer mixture gave a brittle film which must be swelled in water to give an elastic, non-brittle material with an opaque appearance.

The biocompatibility of the preparations according to the invention was demonstrated by the test hereafter described.

EXAMPLE 5

Blood Compatibility Test

Release of $^3$H-serotonin by human platelets was used in preliminary studies to assess the blood reactivity of the product of Example 4. Normal human venous blood was drawn into plastic syringes and immediately transferred to plastic tubes containing 3.8% sodium citrate (one part citrate to nine parts whole blood). Platelet rich plasma was prepared by centrifugation at 4° C. for 15 minutes at 125×g and removed by serological pipet to a plastic or siliconized test tube. $^3$H-serotonin ($^3$H-5-hydroxytryptamine, $^3$H-5HT; New England Nuclear, 26.3 Ci/mmol, 1mCi/ml ethanol-water) was added to platelet rich plasma (PRP), 0.2–0.5 ul/ml PRP, and incubated for 15 minutes at 37° C. In the assay, siliconized or polypropylene test tubes were used; thrombin was used as a positive control, coated and uncoated samples were tested. 1.0–2.0 ml of $^3$H-5HT-PRP was added to each of duplicate tubes containing samples to be assayed; a 50 ul aliquot was removed from the control mixture for determination of total radioactivity. Following the appropriate incubation period (10–120 minutes) 0.2–0.5 ml aliquots of the suspension were removed and centrifuged over silicon oil in an Eppendorf microfuge for two minutes at 12,000×g. 50 ul of the supernatant was removed from each tube, mixed with 5 ml of liquid scintillation fluid, and radioactivity measured by beta-spectrometry. The amount of $^3$H-5HT released by thrombin or the test samples was the increment in radioactivity of the supernatant (radioactivity of experimental samples minus radioactivity control). Coated samples of the product of Example 4 were consistently less reactive in terms of amount of $^3$H-5HT released; uncoated samples induced 52% greater release than the coated samples.

Variations and modifications can, of course, be made without departing from the spirit and scope of the invention.

Having thus described our invention what we desire to secure by Letters Patent and hereby claim is:

1. A composition of matter comprising poly (2-hydroxy ethyl methacrylate) modified by the inclusion therein of hyaluronic acid or a salt thereof.

2. A composition according to claim 1 wherein the included hyaluronic acid is distributed throughout the body and on the surface of the polymeric material.

3. A composition according to claim 2 wherein the hyaluronic acid on the surface of the polymeric material is cross-linked.

4. A formed article made from the composition according to claim 1.

5. An article according to claim 4 which is a casting, a film, a fiber or a fabric.

* * * * *